United States Patent
Welker et al.

(10) Patent No.: US 8,127,625 B2
(45) Date of Patent: Mar. 6, 2012

(54) SIGHT GLASS WITH LIQUID SEPARATOR

(75) Inventors: Brian H. Welker, Fulshear, TX (US); Dennis M. McKay, Richmond, TX (US); Daniel R. Welker, Richmond, TX (US)

(73) Assignee: Welker, Inc., Sugar Land, TX (US)

(*) Notice: Subject to any disclaimer, the term of this patent is extended or adjusted under 35 U.S.C. 154(b) by 330 days.

(21) Appl. No.: 12/572,249

(22) Filed: Oct. 1, 2009

(65) Prior Publication Data
US 2010/0313656 A1    Dec. 16, 2010

Related U.S. Application Data

(63) Continuation-in-part of application No. 12/484,162, filed on Jun. 12, 2009.

(51) Int. Cl.
*G01N 1/22* (2006.01)
(52) U.S. Cl. ..................................... 73/863.21
(58) Field of Classification Search ............... 73/863.21, 73/863.22, 28.04, 28.05; 95/267, 272; 96/413, 96/416
See application file for complete search history.

(56) References Cited

U.S. PATENT DOCUMENTS
6,818,045 B2    11/2004    Welker

OTHER PUBLICATIONS

Welker, Inc., prior art apparatus, Sight Glass—Style SG-3, Oct. 31, 1986.

*Primary Examiner* — Hezron E Williams
*Assistant Examiner* — Jamar Ray
(74) *Attorney, Agent, or Firm* — Husch Blackwell LLP (57) ABSTRACT

A liquid separator with at least one flow passageway is used to detect and remove the presence of entrained liquids from natural gas during spot sampling procedures prior to analysis of the sample by a gas chromatograph. In one embodiment, the at least one flow passageway directs at least a portion of the gas flow to impinge upon the inside surface of a sight glass and swirl around in a chamber which may cause droplets of liquid to coalesce on the inside of the sight glass and may cause a fog to form inside the chamber, all of which make it easier to see the existence of liquids in the natural gas. The at least one flow passageway is less expensive to fabricate than some prior art flow directing elements.

14 Claims, 7 Drawing Sheets

SIGHT GLASS WITH LIQUID SEPARATOR

CROSS REFERENCE TO RELATED APPLICATION

This is a continuation-in-part of U.S. application Ser. No. 12/484,162 filed on Jun. 12, 2009 for "Sight Glass With Flow Directing Assembly."

BACKGROUND OF THE INVENTION

Natural gas may be collected in a portable sample collection vessel and taken to a laboratory for analysis. This technique is often called "spot sampling" in the industry. In the laboratory, the sample is often analyzed to determine the Btu content of the natural gas using a gas chromatograph (GC). The GC is an excellent instrument for analyzing the content of a dry sample of any gas; however this instrument does not do a good job of analyzing a sample that includes fluids.

While spot sampling natural gas, it is important to determine whether the gas is dry or if it has entrained liquids, which is often referred to as "wet gas". U.S. Pat. No. 6,818,045, which is incorporated herein by reference, entitled "Liquid Separator with Integral Sight Glass" assigned to Welker Engineering Company, the predecessor of the present assignee, Welker, Inc. was an apparatus that was intended to show whether the gas was dry or wet as it passed into a sample container during a spot sampling procedure. However, in use, it was difficult for the field technician to accurately determine whether the gas was dry or wet using the apparatus disclosed in the '045 Patent. There is still a need in the industry for an economical and simple way to determine whether gas is wet or dry while spot sampling.

Welker Engineering Company (Now Welker, Inc.) has previously sold a sight glass without a filter or a drain, called the model SG3. The SG3 sight glass was primarily used with odorant injection systems to provide visual confirmation that the odorant was being properly injected into the system. The SG3 was also used to provide visual confirmation in chemical injection systems that use glycol. In some situations, the SG3 has been used at a spot sampling station to visually determine if liquid was being transferred into a sample cylinder. The SG3 did not prevent liquids from entering a sample cylinder nor did it have a flow directing assembly.

Welker, Inc. has also previously sold a filter without a sight glass called the LE2. The LE2 filter has been used at spot sampling stations to keep liquids out of sample cylinders. However, the LE2 filter did not provide any visual information to the personnel that were taking the spot sample.

Other companies, such as A+Corporation of Prairieville, La. also sell liquid separators and filters to keep liquids out of sample cylinders at spot sampling stations. Some of these products from A+ are described in the company web site (www.apluscorporation.com), but none have a flow directing assembly. In summary, the prior art filters and liquid separators from Welker and A+ do not incorporate a sight glass or a flow directing element. There is still a need in the industry for improved equipment to detect entrained liquids in natural gas.

SUMMARY OF THE INVENTION

The present invention is a sight glass to be used during spot sampling of natural gas at pressures of up to 2000 psi, to determine if the gas is wet or dry. The sight glass includes a first transparent window that in conjunction with the end caps defines a chamber through which the natural gas passes prior to being captured in a sample container. The first transparent window must be capable of withstanding the operating pressure of the natural gas that is being sampled. The flow directing assembly causes at least a portion of the natural gas to impinge upon the inside surface of the first transparent window which makes it easier to see from the outside by a sampling technician.

In one embodiment, the first transparent window is cylindrical and the flow directing assembly includes three hollow risers that are curved causing the gas flow to impinge upon and swirl around the inside cylindrical surface of the first transparent window which in some instances causes droplets to form on the inside surface of the first transparent window when wet gas is being sampled. These droplets are conspicuous and easy to see by a spot sampling technician. The swirling action also sometimes causes a fog to form in the chamber which also is conspicuous and easy to see by a spot sampling technician.

In one embodiment, a replaceable membrane acts to separate liquid, if any, from the gas as it impinges and swirls around the chamber. In several embodiments, the chamber acts as a liquid collection vessel. From time to time, a valve may be opened to drain accumulated liquids from the chamber.

In other embodiments at least one flow passageway is substituted for the flow directing assembly of the prior embodiments. The at least one flow passageway is less expensive and faster to make than the flow directing element.

DETAILED DESCRIPTION OF THE INVENTION

Figure 1:
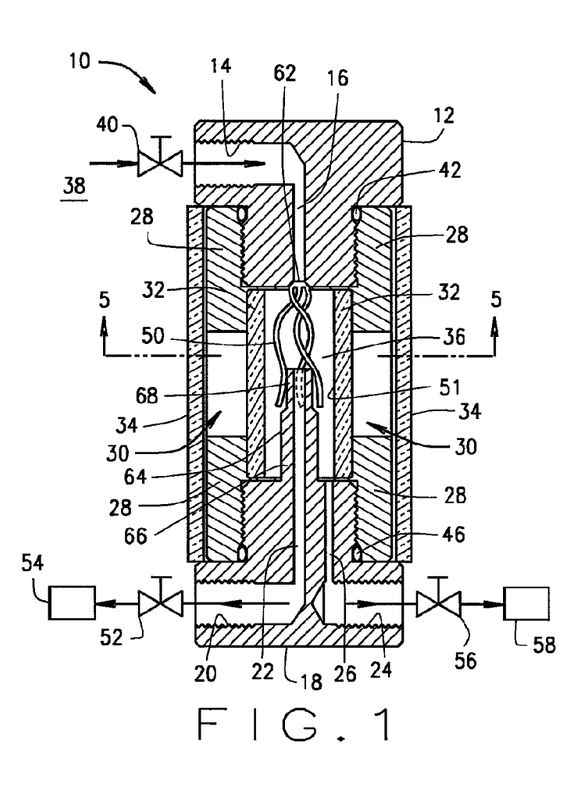
FIG. 1 is a section of a sight glass with an open ended elongate riser.

FIG. 1 is a section view of a sight glass generally identified by the numeral 10. A top cap 12 defines an inlet 14 and an inlet at least one passageway 16. A bottom cap 18 defines an outlet 20 and an outlet at least one passageway 22. The bottom cap further defines a drain 24 and a drain at least one passageway 26. A body 28 defines a viewing slot 30. The body threadably engages the top cap and bottom cap. A first transparent window 32 is captured between the top and bottom caps. A second transparent window 34 is also captured between the top and bottom caps.

The first transparent window 32 may be formed from glass. One brand of glass that may be suitable is Gold Dot brand tempered glass from Corning of Corning, N.Y. Other brands of glass may be suitable for use in this invention provided they are capable of withstanding the operating pressure of the fluids that pass through the apparatus which may reach 2,000 psi or more. The second transparent window 34 may be formed from plastic. One brand of plastic that may be suitable for forming the second transparent window is Plexiglas® brand thermoplastic poly (methylmethacrylate)-type polymers sold by Rhom and Haas Company of Philadelphia, Pa.

In combination the top cap, bottom cap and the first transparent window define a chamber 36. Natural gas and perhaps entrained fluids from a natural gas source 38 pass through an inlet valve 40 to the inlet 14, through the inlet at least one passageway 16 and into the chamber 36. An outside observer may look through the second transparent window 34, the viewing slot 30 and the first transparent window 32 into the chamber 36 to see whether any entrained liquids are present. An O-ring 42 seals the top cap against the body. A second O-ring 46 seals the bottom cap against the body.

Figure 4:
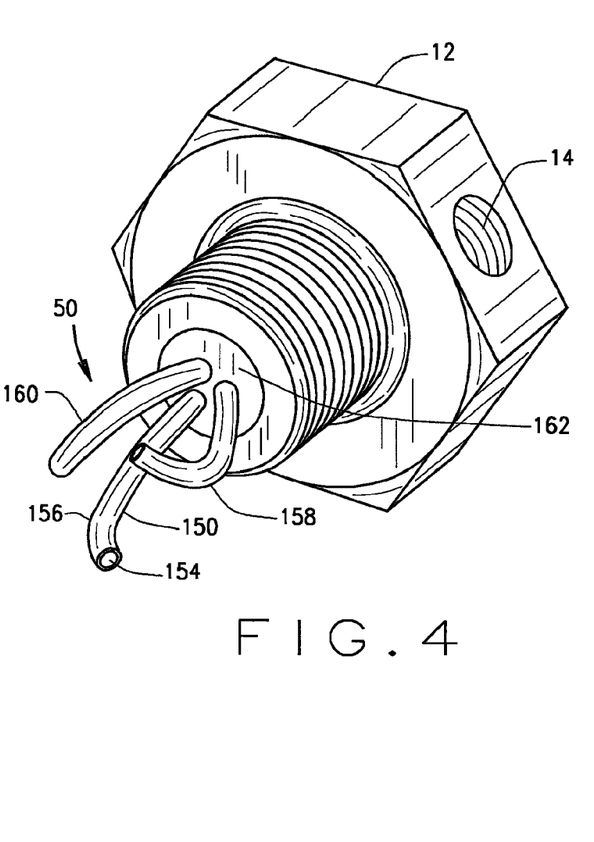
FIG. 4 is a perspective view of one embodiment of a flow directing assembly.

The flow directing assembly 50 is in fluid communication with the inlet and the inlet at least one passageway to direct at least a portion of the natural gas to impinge upon the inside surface 51 of the first transparent window 32 surrounding the chamber 36 to make it easier for an outside observer to detect whether there are liquids present in the natural gas. One embodiment of the flow directing assembly is better seen in FIG. 4. In FIG. 4, the flow directing assembly is angled to cause the natural gas to swirl about in the chamber which may be cylindrical as shown in FIG. 1.

In FIG. 1, the natural gas exits the chamber and passes through the outlet at least one passageway 22, through the outlet valve 52 into a removable sample collection apparatus 54. When captured in the sample collection apparatus the natural gas and any entrained liquids are referred to in the industry as a "sample".

The removable sample collection apparatus is an off the shelf item and may be purchased in many different configurations from many different vendors, as is well known to those skilled in the art. Once filled, the sample collection apparatus may be taken to a laboratory to analyze the sample. But if the natural gas is found to have entrained liquids while the sample is being taken, it may be discarded. In the alternative, the sample collection apparatus with a wet sample will be tagged so the lab may take precautions not to injure the GC. Yet another alternative is to bring a portable separator to the well or other location to strip out the liquids.

In the past, it was common to build large "stripper" plants in a gas field to separate the liquids from the natural gas. As a result, most pipelines transported dry gas. Today, gas fields are smaller and large stripper plants are becoming less common. Some smaller portable separators are available, but they are not used on all wells or pipelines. Therefore, wet gas is encountered with more frequency today than in years past.

A drain valve 56 is in fluid communication with the drain at least one passageway 26 and a liquid collecting apparatus 58. If liquids collect in the chamber 36, the drain valve 56 may be opened to drain liquids from the chamber through the drain at least one passageway into the liquid collecting apparatus, thus discouraging liquids entering the at least one passageway 22.

The flow directing assembly 50 is connected to the outlet port 62 of the inlet at least one passageway 16. In this embodiment, all the natural gas that flows through the sight glass 10 also flows through the flow directing assembly 50 to better determine whether entrained liquids exist in the natural gas.

A hollow elongate riser 64 extends from the bottom cap into the chamber 36. The hollow elongate riser 64 may be integral with the bottom cap, as shown, or it may be a separate member that threadably engages the bottom cap, not shown in this figure. The proximal end 66 of the elongate riser 64 is in fluid communication with the outlet at least one passageway 22 and the distal end 68 is in fluid communication with the chamber 36.

Natural gas flows through the inlet 14, the inlet at least one passageway 16, and the flow directing assembly 50 into the chamber 36. In one embodiment, the natural gas impinges the inside surface 51 of the first transparent window 32 and swirls around in the chamber 36. Liquids, if any may appear on the inside surface 51 of the first transparent window 32, as droplets and/or a fog inside the chamber itself. Liquids may also be separated from the natural gas in the chamber 36. The natural gas then leaves the chamber and passes through the hollow elongate riser 64, the outlet at least one passageway 22, the outlet 20, and the outlet valve 52 into the sample collection apparatus 54, while liquids are encouraged to exit through at least one passageway 26.

Figure 2:
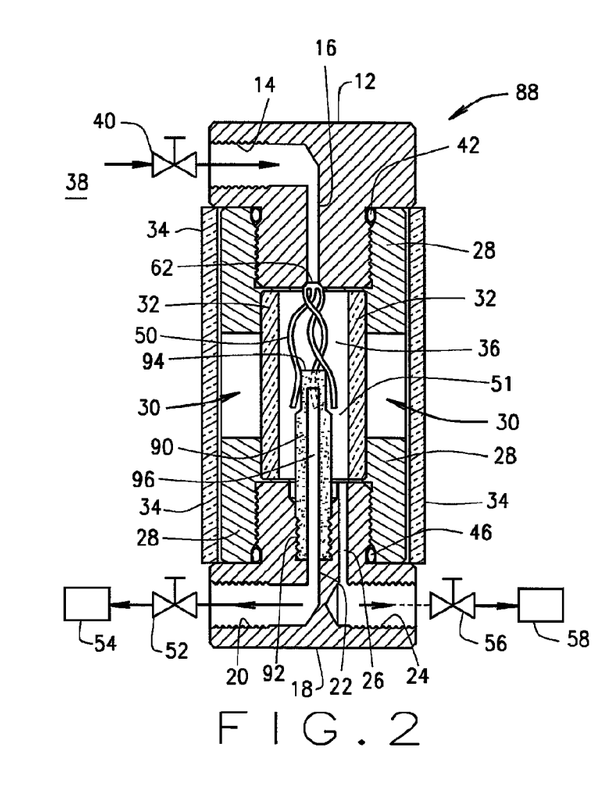
FIG. 2 is a section view of an alternative embodiment of the sight glass of FIG. 1 with an elongate riser formed from porous sintered metal.

FIG. 2 is a section view of an alternative embodiment of the sight glass 88 with an elongate riser 90 formed from porous sintered metal. The elongate riser 90 has a proximal end 92 which threadably engages the bottom cap 18. The elongate riser 90 has a distal end 94 which is closed. The center 96 of the elongate riser 90 is otherwise open and in fluid communication with the outlet passage 22. Except for the riser 90, the sight glass 88 of FIG. 2 is similar to the sight glass shown in FIG. 1 and common components have common numbers. The purpose of the sintered elongate riser 90 is to act as a particulate filter for the natural gas. The sintered elongate riser 90 will pass some liquids and all gases, but not particles.

Figure 3:
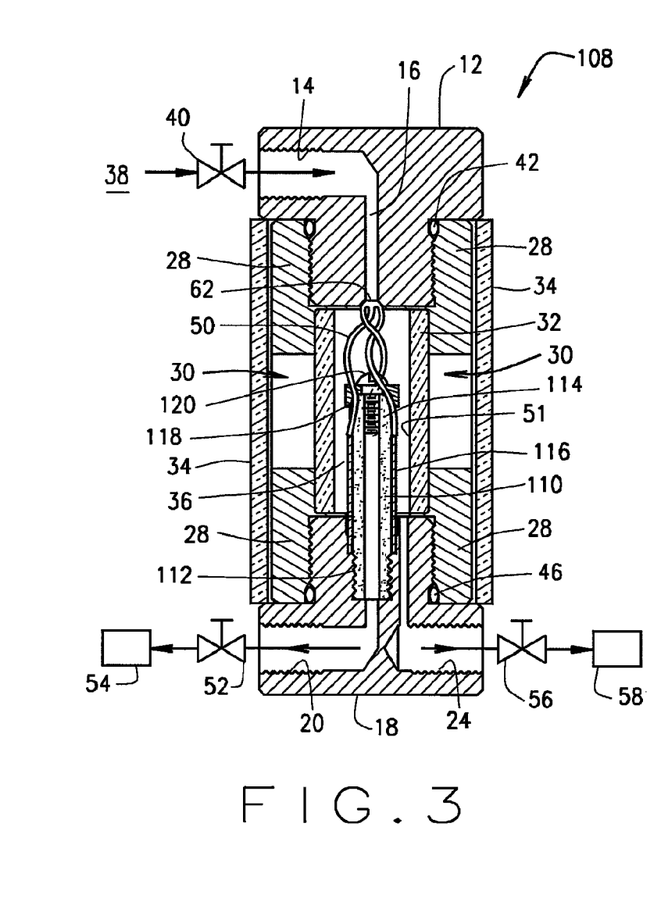
FIG. 3 is a section view of a sight glass of an alternative embodiment of the sight glass of FIG. 1 with a replaceable membrane filter to separate liquid, if any from the gas.

FIG. 3 is a section view of an alternative embodiment of the sight glass 108 with a replaceable membrane to separate liquid, if any from the gas. The hollow sintered metallic riser 110 has an open proximal end 112 that threadably engages the bottom cap 18 and an open distal end 114. A membrane filter 116 is sized and arranged to fit over a portion of the hollow sintered metallic riser. The membrane filter may be formed from Teflon® brand tetrafluoroethylene fluorocarbon polymer produced by Du Pont de Nemours, E.I. Company. However, other membranes may be suitable in this invention provided that they achieve separation of gas from liquids. For example, Tyvek® brand material also from Du Pont may also be suitable as well as Millipore four micron filter paper from Pall Specialty materials, of Charlotte, N.C. and/or cat gut may also be suitable. The only requirement for the membrane is that it be gas permeable and substantially impermeable to liquids. A cap 118 is sized and arranged to fit over the distal end 114 of the hollow sintered metallic riser 110 to hold the membrane filter 116 in place. A screw 120 threadably engages the distal end 114 of the hollow sintered metallic riser and captures the cap on the riser. The cap holds the membrane filter 116 in place.

FIG. 4 is a perspective view of one embodiment of a flow directing assembly generally identified by the numeral 50. A first tubular member 150 has a tubular inlet, not shown, and a tubular outlet 154 both in fluid communication with the inlet 14 and inlet at least one passageway 16. The tubular member 150 is curved at 156 to cause the natural gas and entrained liquids, if any, to impinge upon the inside surface 51 of the first transparent window 32 to make it easier for an outside observer to see entrained liquids in the natural gas flowing through the sight glass 10, 88 or 108. The purpose of the curved tubular member 150 is to cause the natural gas and entrained liquids, if any, to impinge upon the inside surface 51 and swirl about the chamber 36. As previously mentioned in some situations, this may form droplets of liquid on the inside surface 51 and otherwise may cause a fog to appear in the chamber 36, both of which are easy to see by an outside observer.

A second tubular member 158 and a third tubular member 160 are welded together at 162 into the outlet port 62 of the inlet at least one passageway 16. The outlet port 62 is better seen in the preceding figures. The flow directing assembly 50 includes at least one tubular member and in the preferred embodiment includes at least three tubular members, as shown in FIG. 4. The flow directing assembly directs at least a portion of the flow of natural gas from the inlet port 14; in the embodiment shown in FIG. 4 all the flow of natural gas from the inlet port 14 is being directed through the flow directing assembly 50.

Figure 5:
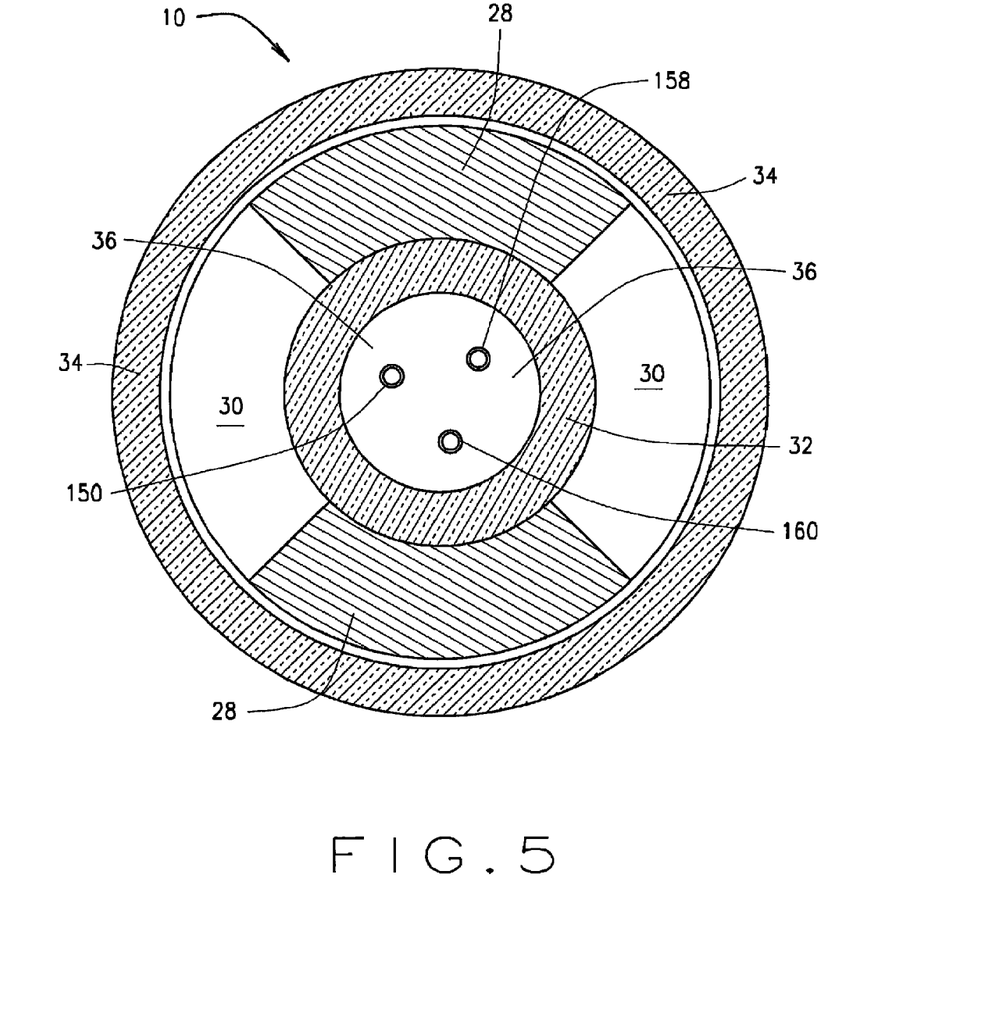
FIG. 5 is a section view of the sight glass of FIG. 1 along the line 5-5.

FIG. 5 is a section view of the sight glass 10 of FIG. 1 along the line 5-5. The second transparent window 34 surrounds the body 28 which defines a viewing slot 30. The sampling technician looks through the second transparent window 34, through the viewing slot 30 through the first transparent window 32 into the chamber 36 to determine the presence of liquids, if any, in the natural gas. The first tubular member 150, the second tubular member 158 and the third tubular member 160 are seen in section view. The first transparent window 32 may be formed from high strength glass to withstand the pressures of the natural gas, which may reach up to 2,000 psi. The body 28 is typically formed from metal and the second transparent window may be formed from plastic and acts as a shield.

Figure 6:
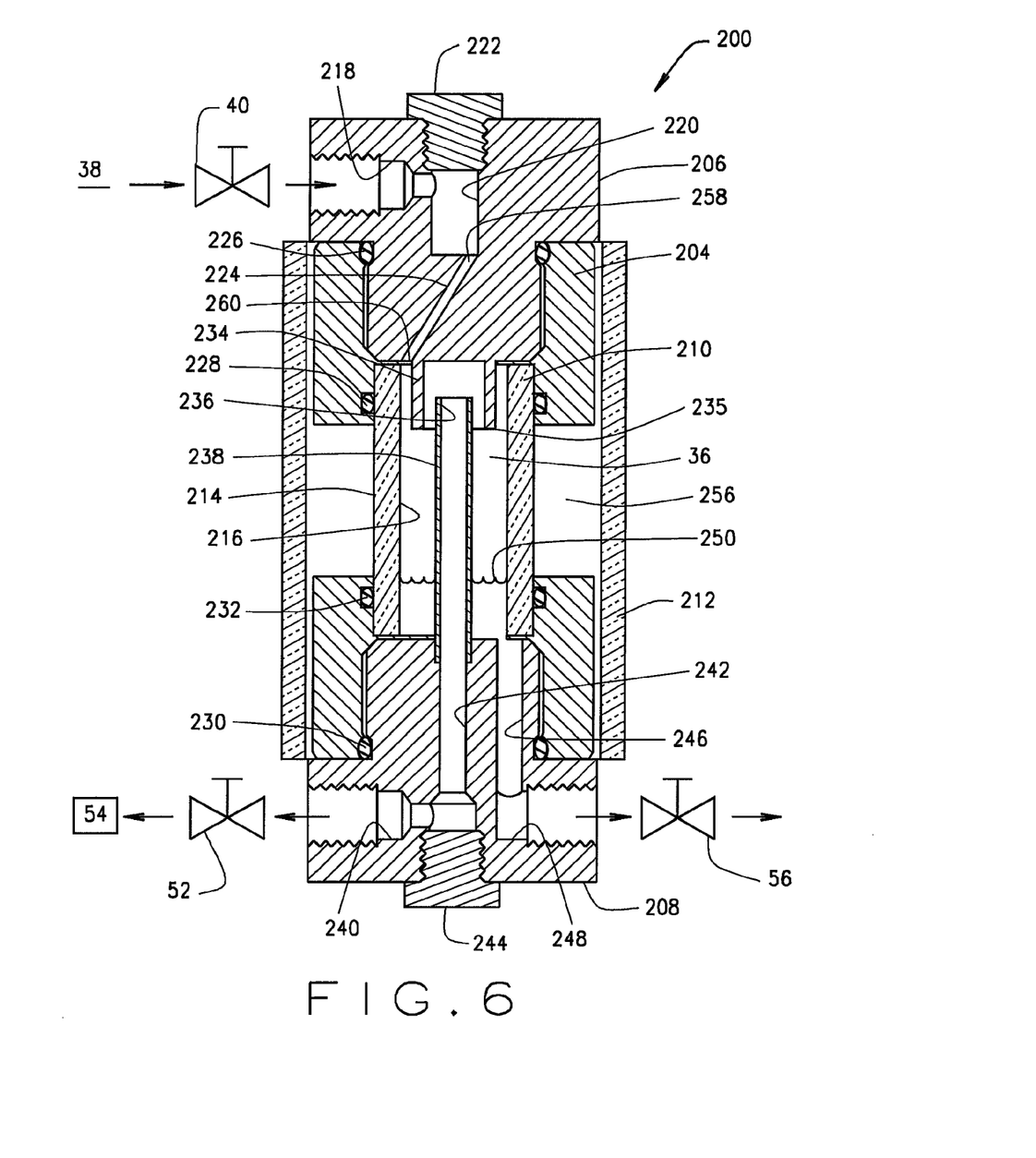
FIG. 6 is a section view of an alternative embodiment of a sight glass with liquid separator. This embodiment does not have the flow directing assembly of FIGS. 1-5.

FIG. 6 is a section view of an alternative embodiment of a sight glass with liquid separator 200 which is more economical to manufacture than any of the previous embodiments shown in FIGS. 1-5. Components that are similar to the previous embodiments may be given the same identification numerals. The primary difference between the embodiments of FIGS. 6-11 is the use of at least one passageway 224 in lieu of the flow directing assembly 50. The flow directing assembly 50 is time consuming and expensive to make. The at least one passageway 224 is less expensive and faster to fabricate. Therefore, the embodiments in FIGS. 6-11 are less expensive to fabricate than the embodiments of FIGS. 1-5 and the embodiments in FIGS. 6-11 have at least the same or better functional attributes as the embodiments of FIGS. 1-5.

A body 204 threadably engages a top cap 206 and a bottom cap 208. A sight glass 210 is captured in the body between the top cap and the bottom cap. The sight glass, the top cap and the bottom cap define the chamber 36. A shield 212 surrounds at least a portion of the body and the sight glass, protecting the sight glass from damage by foreign objects. The sight glass 210 defines an outside surface 214 and an inside surface 216. The sight glass and the shield are transparent. The sight glass 210, like the first transparent window 32, may be formed from high strength glass to withstand the pressures from the natural gas inside the chamber 36. The shield 212, like the second transparent window 34, may be formed from plastic.

The source of natural gas 38 is in fluid communication with the inlet valve 40 which is in fluid communication with an inlet 218. A bore 220 is located along the centerline of the top cap and is sealed by a plug 222. The at least one passageway 224 connects the inlet and the bore 220 to the chamber 36. The at least one passageway 224 shown in FIG. 6 is solely for illustrative purposes and is not a true cross section of the device as explained below.

The at least one passageway 224 takes the place of the flow directing assembly 50 which is expensive and time consuming to construct. The at least one passageway 224 is produced with a mill and the at least one passageway is drilled into the top cap. The at least one passageway 224 is in fluid communication with the source of natural gas 38, the inlet 218, the bore 220 and the chamber 36. The source of natural gas 38 may be "wet" gas that may have entrained liquids.

The chamber 36 is sealed against atmosphere by a first O-ring 226, a second O-ring 228, a third O-ring 230 and a fourth O-ring 232. A hollow shroud 234 extends from the top cap into the chamber 36 and is proximate the riser 238 which extends from the bottom cap. In one embodiment, the tip 235 of the shroud 234 surrounds and extends beyond the inlet 236 of the riser. In other embodiments, not shown, the tip 235 of the shroud 234 may be recessed from the inlet 236 of the riser. In the alternative, the inlet 236 of the riser 238 may be level with the tip 235 of the shroud 234. All that is necessary is that the inlet 236 of the riser 238 be proximate the tip 235 of the shroud 234.

A removable sample container 54 is in fluid communication with an outlet valve 52 and the outlet 240. A bore 242 is formed along the centerline of the bottom cap 208 and is sealed by a plug 244. The riser 238 may be welded in the bore 242 allowing fluid to flow from the chamber 36, through the riser 238, the bore 242, the outlet 240, and the outlet valve 52 to the removable sample cylinder 54. The riser 238 may also be threadably attached to the bottom cap 208.

Another bore 246 is made in the bottom cap and is in fluid communication with the drain 248. The drain is in fluid communication with the drain valve 56. As indicated by the fluid level line 250, fluids may collect in the bottom of the chamber 36 and may be drained from the chamber 36 by opening the drain valve 56. These fluids may fall on the ground, may vaporize upon hitting the atmosphere or may be collected in some other container, not shown. Prior to taking a spot sample it is advisable to open the drain valve 56 and clear any accumulated fluids in the chamber 36. If after draining the chamber 36, additional liquids are observed in the chamber or on the inside surface of the sight glass 210 while taking a spot sample, the presence of such additional liquids should be reported to the lab.

Figures 7, 8, 9:
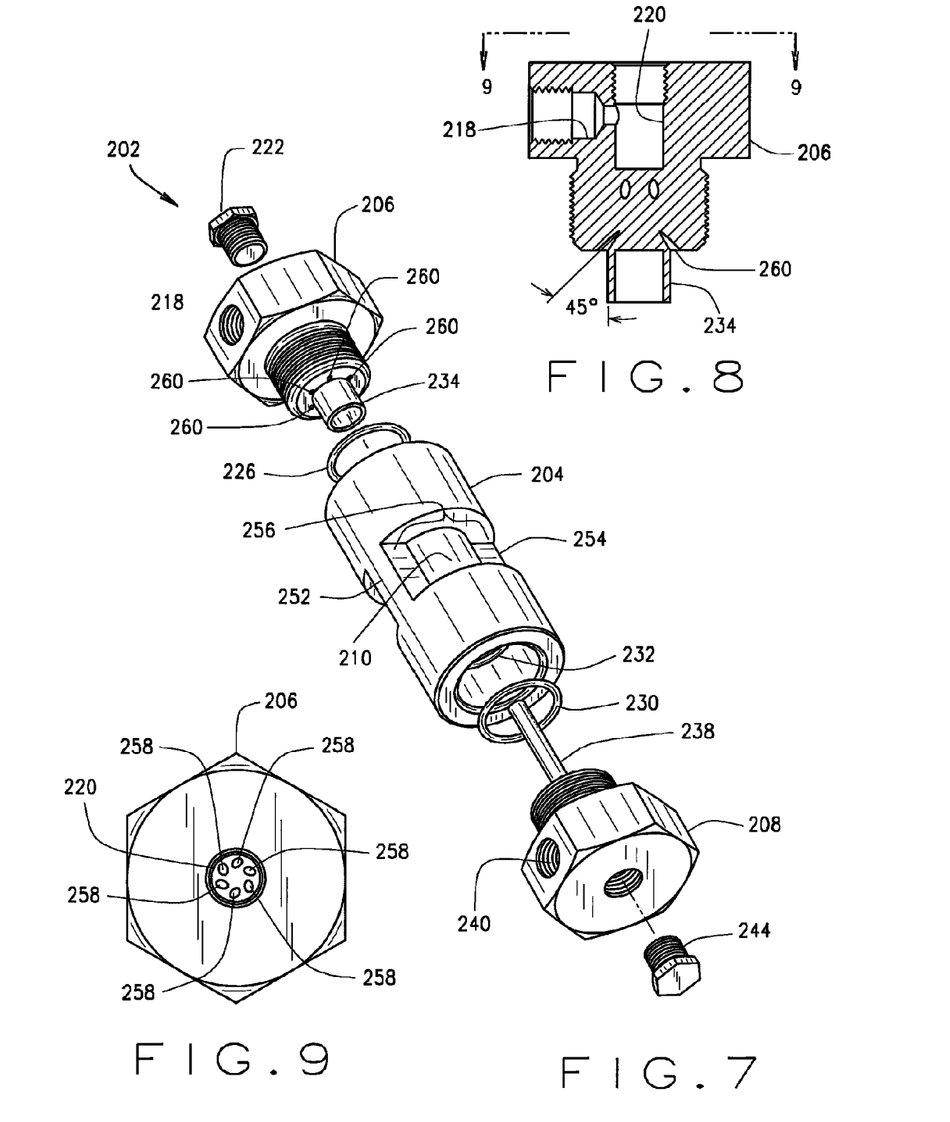
FIG. 7 is an exploded view of the sight glass with liquid separator of FIG. 6.
FIG. 8 is a section view of the top cap from the sight glass with liquid separator of FIG. 6.
FIG. 9 is a plan view of the top cap from the sight glass with liquid separator.

FIG. 7 is an exploded view of the sight glass with liquid separator 200 of FIG. 6. The body 204 forms a first bar 252 and an opposing bar 254 which define a cutout which serves as a window 256 for the observer, not shown, to look through the transparent sight glass 210 into the chamber 36 to determine the presence of liquids, if any.

FIG. 8 is a true section view of the top cap 206 and FIG. 9 is a plan view of the top cap 206 taken along the line 9-9 of FIG. 8. In one embodiment, the at least one passageway 224 is formed as a plurality of passageways, each having at least one passageway inlet 258, as best seen in FIG. 9 and each having at least one passageway outlet 260 as best seen in FIG. 7. As previously mentioned, one way to form the at least one passageway 224 is to use a mill and a drill bit. The shroud 234 of the top cap 206 is first oriented at approximately a 45° angle from the work table of the mill. The purpose of the approximate 45° angle is to cause the stream of natural gas to impact the inside surface 216 of the sight glass 210 when the drain valve 56 is open. The drill bit is then offset at approximately 11° from the centerline of the head to bore each at least one passageway. The purpose of the approximate 11° angle is to cause the stream of natural gas to swirl around the inside of the sight glass when the drain valve is open, prior to taking a spot sample. This technique is referred to drilling at compound angles and is well known to those skilled in the art of using a mill. The at least one passageway 224 may, in the alternative, be formed by electronic discharge machining (EMD), laser micro drilling or water blasting, among other techniques. The inlet 258 of the at least one passageway 224 connects to the bore 220 and the outlet 260 is positioned between the outside of the shroud and the inside surface 216 of the sight glass.

The at least one passageway 224 may be formed with two acute angles as previously mentioned. One acute angle is good, but two acute angles are even better. The first angle, approximately 45° is shown in FIG. 8. As previously mentioned, the purpose of the approximate 45° angle is to cause the stream of natural gas to impact the inside surface 216 of the sight glass 210 when the drain valve 56 is open. This acute angle makes it easier to see the presence of entrained liquids, if any, in the natural gas and to encourage the liquids to coalesce on the inside surface of the sight glass in the chamber 36. Any acute angle is believed to be suitable for use in this invention.

Figure 12:
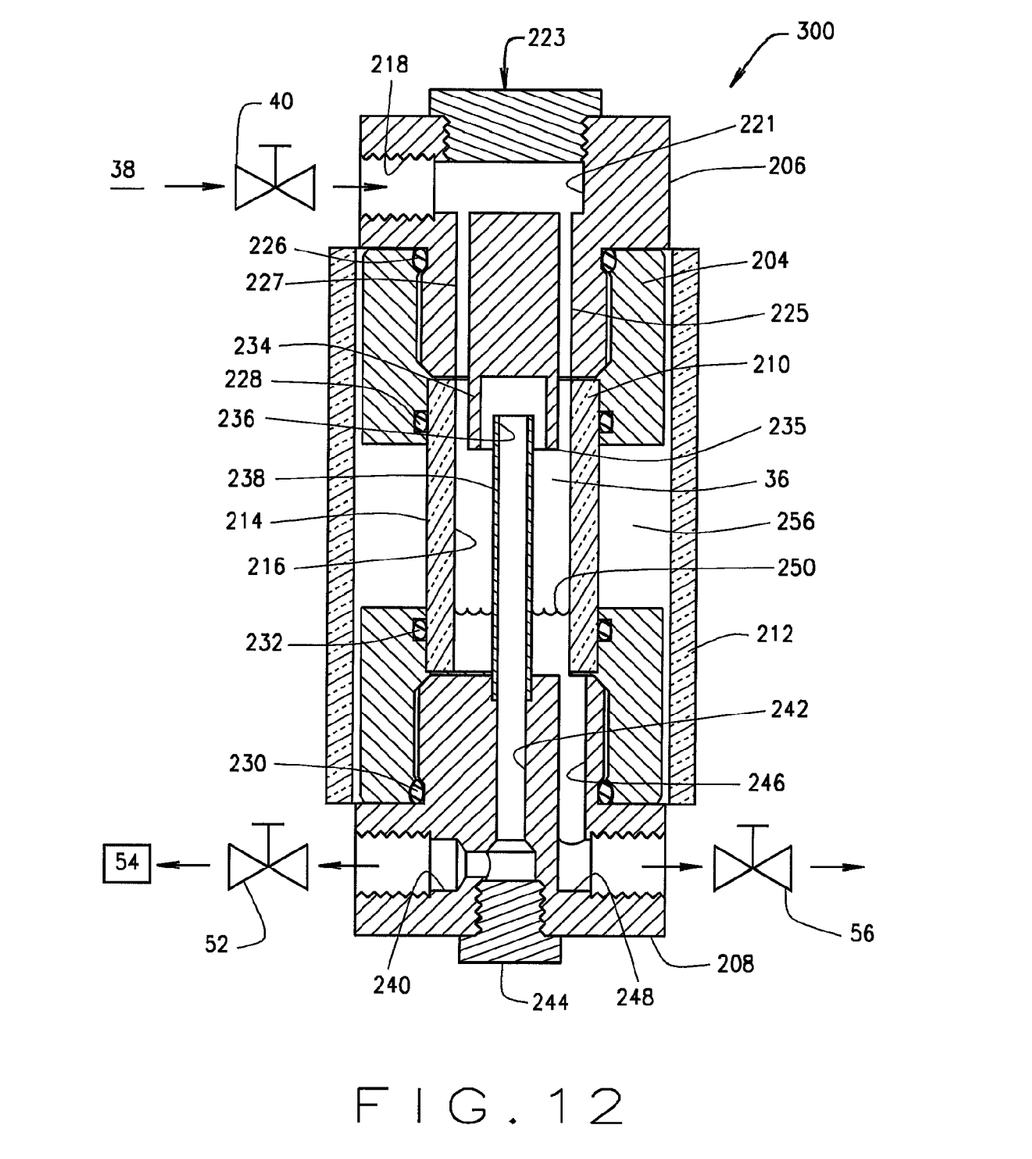
FIG. 12 is a section view of the sight glass with liquid separator, similar to FIG. 6, except the passageways into the chamber are different.

The second angle is approximately 11° and is best seen in FIG. 8 which is a true section view. As previously mentioned, the purpose of the approximate 11° angle is to cause the stream of natural gas to swirl around the inside of the sight glass when the drain valve is open, prior to taking a spot sample. This acute angle also makes liquids, if any, easier to see and encourages them to coalesce or form a "fog" inside the chamber. Any acute angle is suitable for use in this invention. The two acute angles described above are the best mode known to the inventors at the time of filing, but other acute angles are also suitable for use in this invention. Further, the diameter of the at least one passageway is not critical to the success of this apparatus. The use of compound acute angles is not critical to the success of this apparatus. All that is critical is for at least one passageway to be formed between the inlet 218 and the chamber 36 to allow natural gas and entrained liquids, if any, to flow into the chamber 36. FIG. 12 is an example of a passageway without any acute angles.

Figure 10:
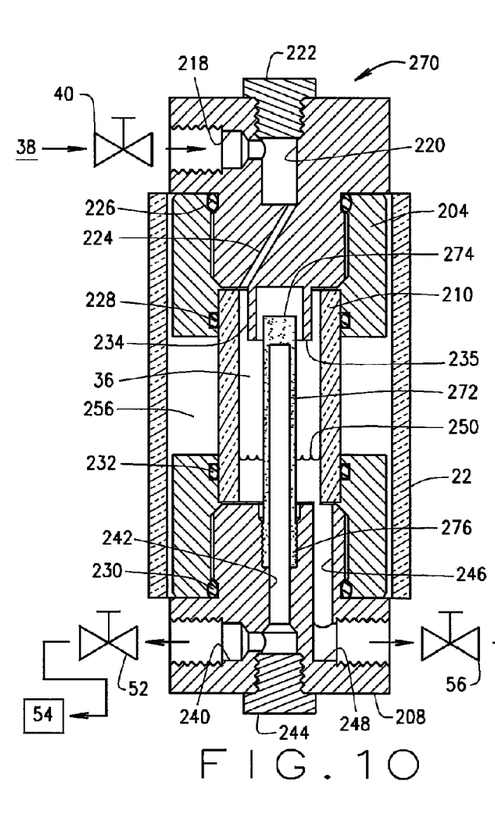
FIG. 10 is an alternative embodiment of the sight glass with liquid separator having a sintered riser.

FIG. 10 is a section view of an alternative embodiment of the sight glass with liquid separator 270, which is similar to the apparatus in FIG. 6 with one exception. In FIG. 6, the riser 238 is formed from tubular metal. In FIG. 10, the riser 272 is formed from sintered metal. The purpose of the riser 272 is to act as a particulate filter for the natural gas. The sintered elongate riser 272 will pass some liquids and all gases, but not particles. The hollow sintered metallic riser 272 is closed on one end 274 and is open on the other end 276. The open end 276 is in fluid communication with the bore 242 and the outlet 240. The hollow sintered metallic riser 272 extends from the bottom cap 208. The hollow sintered metallic riser 272 may be welded to the bottom cap, may threadably engage the bottom cap, or it may otherwise be connected to the bore 242. In FIG. 10 the sight glass with liquid separator is shown with a shroud 234. However, the shroud 234 is optional in this embodiment.

Figure 11:
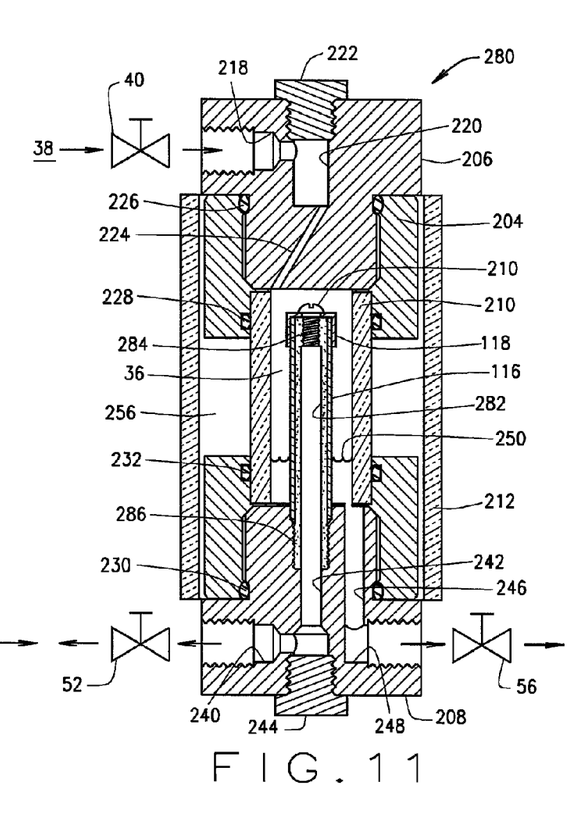
FIG. 11 is an alternative embodiment of the sight glass with liquid separator having a sintered riser and membrane filter.

FIG. 11 is a section view of an alternative embodiment of the sight glass with liquid separator 280 which is similar to the apparatus in FIG. 3, except there is no flow directing assembly 50. Common components may be given common parts numbers.

In FIG. 11, at least one passageway 224 directs the natural gas with entrained liquids, if any, from the inlet 218 to the chamber 36. As previously explained, the at least one flow directing passage 224 is faster to manufacture and less expensive than the previous flow directing element 50. A sintered metallic riser 282 is surrounded by a removable membrane filter 116 that is held in place by a screw 210 and a cap 118. This membrane filter 116 may be fabricated from the same materials, previously discussed. The membrane filter 116 must be permeable to gases and substantially impermeable to liquids and it must be compatible with typical natural gas liquids, such as liquid butane, liquid propane, liquid isobutane, natural gasoline, etc. The screw engages a first open end 284 of the sintered metallic riser 282. A second open end 286 of the sintered metallic riser 282 engages the bottom cap 208. The sintered metallic riser may be welded into the bottom cap, threaded into the bottom cap or connected by other means.

FIG. 12 is a true section view of an alternative embodiment of the sight glass with liquid separator 300 similar to the version in FIG. 6, except the flow passageways in the top cap 206 are formed in a different manner. A large bore 221 is formed in the top cap and is sealed by a plug 223. The bore 221 is in fluid communication with the inlet 218. An at least one passageway 227 is formed in the top cap 206 and is in fluid communication with the inlet 218 and the chamber 36. The at least one first flow passageway is formed parallel to the centerline of the top cap and enters the chamber 36 between the outside of the shroud 234 and the inside surface 216 of the sight glass 210. There is no angle, in the at least one passageway 227. A second passageway 225 is formed in the top cap, opposite the passageway 227. In this embodiment there are a plurality of flow passageways that surround the shroud 234, two of which are shown, 227 and 225 in this figure. This angle free alternative allows fluid communication between the source of natural gas 38, the inlet 218, the bore 221 and the chamber 36. But in the inventors' opinion the at least one passageway should have at least one acute angle or even better compound acute angles described in FIGS. 6-11 making it easier for an observer, not shown, to see the presence of liquids, if any, in the chamber 36. The sight glass with liquid separator in all embodiments, 200, 270, 280 and 300 needs to be properly oriented so gravity can work on the liquids, if any. The top cap 206 should be further away from the earth than the bottom cap 208 when properly oriented.

The invention claimed is:

1. A liquid separator in fluid communication with a source of natural gas having entrained liquids and a removable sample container, the liquid separator comprising:
   a body sized and arranged to receive a top cap, a bottom cap, and a transparent sight glass having an outside surface and an inside surface;
   a chamber defined by the body, the inside surface of the transparent sight glass, the top cap and the bottom cap;
   the top cap defining an inlet in fluid communication with the source of natural gas, a hollow shroud extending from the top cap into the chamber and at least one passageway in fluid communication with the chamber, the at least one passageway extending from the inlet to an outlet port located between the inside surface of the transparent sight glass and the shroud;
   the bottom cap defining a sample outlet in fluid communication with the chamber and the removable sample container, a liquid outlet in fluid communication with the chamber and a drain, and a riser in fluid communication with the sample outlet extending from the bottom cap into the chamber, the riser having an inlet port that is proximate with the hollow shroud to retard liquids entrained in the natural gas from entering the riser; and
   opposing windows formed in the body to allow an observer to look through the transparent sight glass into the chamber to determine the presence of liquids.

2. The liquid separator of claim 1 further including a transparent shield surrounding at least a portion of the sight glass.

3. The liquid separator of claim 2 wherein the at least one passageway is angled towards the inside surface of the sight glass causing entrained liquids in the natural gas to contact the inside surface of the sight glass, making them easier to be seen by the observer.

4. The liquid separator of claim 3 wherein the at least one passageway is tilted away from the centerline of the top cap causing the entrained liquids in the natural gas to swirl around inside the chamber, making them easier to be seen be seen by the observer.

5. A liquid separator in fluid communication with a source of natural gas having entrained liquids, and a removable sample container, the liquid separator comprising:
    a body sized and arranged to receive a top cap, a bottom cap, and a transparent sight glass having an outside surface and an inside surface;
    a chamber defined by the body, the inside surface of the transparent sight glass, the top cap and the bottom cap;
    the top cap defining an inlet in fluid communication with the source of natural gas, and at least one passageway in fluid communication with the chamber extending from the inlet to an outlet port located between the transparent sight glass and a shroud extending from the top cap;
    the bottom cap defining a sample outlet in fluid communication with the chamber and the removable sample container, a liquid outlet in fluid communication with the chamber and a drain, and a sintered riser in fluid communication with the chamber, the sample outlet and the removable sample container extending from the bottom cap into the chamber;
    the sintered riser being hollow and having a closed end in the chamber and an open end in fluid communication with the sample outlet; and
    opposing windows formed in the body to allow an observer to look through the transparent sight glass into the chamber to determine the presence of liquids.

6. The apparatus of claim 5 further including the shroud extending from the top cap into the chamber proximate with the sintered riser.

7. The liquid separator of claim 6 further including a transparent shield surrounding at least a portion of the sight glass.

8. The liquid separator of claim 7 wherein the at least one passageway is angled towards the inside surface of the sight glass causing entrained liquids in the natural gas to contact the inside surface of the sight glass, making them easier to be seen by the observer.

9. The liquid separator of claim 8 wherein the at least one passageway is tilted away from the centerline of the top cap causing the entrained liquids in the natural gas to swirl around inside the chamber, making them easier to be seen be seen by the observer.

10. A liquid separator in fluid communication with a source of natural gas having entrained liquids and a removable sample container, the liquid separator comprising:
    a body sized and arranged to receive a top cap, a bottom cap, and a transparent sight glass having an outside surface and an inside surface;
    a chamber defined primarily by the body, the inside surface of the transparent sight glass, the top cap and the bottom cap;
    the top cap defining an inlet in fluid communication with the source of natural gas, and at least one passageway extending from the inlet to an outlet port in fluid communication with the chamber;
    the bottom cap defining a sample outlet in fluid communication with the chamber and the removable sample container, a liquid outlet in fluid communication with the chamber and a drain;
    a filter assembly positioned in the chamber and in fluid communication with the outlet, the filter assembly separating entrained liquids from the natural gas whereby substantially dry gas passes from the chamber to the removable sample container;
    the filter assembly having;
        a membrane that is permeable to gas and substantially impermeable to liquids and
        a porous elongate riser to support the membrane; and
    opposing windows formed in the body to allow an observer to look through the transparent sight glass into the chamber to determine the presence of liquids.

11. The liquid separator of claim 10 further including a transparent shield surrounding at least a portion of the sight glass.

12. The liquid separator of claim 11 wherein the at least one passageway is angled towards the inside surface of the sight glass causing entrained liquids in the natural gas to contact the inside surface of the sight glass, making them easier to be seen by the observer.

13. The liquid separator of claim 12 wherein the at least one passageway is tilted away from the centerline of the top cap causing the entrained liquids in the natural gas to swirl around inside the chamber, making them easier to be seen be seen by the observer.

14. The apparatus of claim 13 wherein the membrane is foamed from polytetrafluoroethylene.

* * * * *

UNITED STATES PATENT AND TRADEMARK OFFICE
CERTIFICATE OF CORRECTION

| | | |
|---|---|---|
| PATENT NO. | : 8,127,625 B2 | Page 1 of 1 |
| APPLICATION NO. | : 12/572249 | |
| DATED | : March 6, 2012 | |
| INVENTOR(S) | : Brian H. Welker | |

It is certified that error appears in the above-identified patent and that said Letters Patent is hereby corrected as shown below:

Claim 14, Col. 10, Line 47, delete "foamed" and replaced with -- formed --

Signed and Sealed this
Ninth Day of October, 2012

David J. Kappos
*Director of the United States Patent and Trademark Office*